(12) United States Patent
Wong et al.

(10) Patent No.: US 12,029,536 B2
(45) Date of Patent: Jul. 9, 2024

(54) DEVICE AND METHOD SUITABLE FOR MONITORING ARTERIAL BLOOD IN A BODY PART

(71) Applicant: Well Being Digital Limited, Shatin (HK)

(72) Inventors: Ming Yip Wallace Wong, Hong Kong (CN); Chor Tin Ma, Hong Kong (CN)

(73) Assignee: WELL BEING DIGITAL LIMITED, Hong Kong (HK)

( * ) Notice: Subject to any disclaimer, the term of this patent is extended or adjusted under 35 U.S.C. 154(b) by 549 days.

(21) Appl. No.: 16/390,142

(22) Filed: Apr. 22, 2019

(65) Prior Publication Data

US 2019/0298196 A1    Oct. 3, 2019

Related U.S. Application Data

(63) Continuation of application No. 14/432,471, filed as application No. PCT/CN2014/082722 on Jul. 22, 2014, now Pat. No. 10,314,499.

(30) Foreign Application Priority Data

Jul. 18, 2014    (HK) ................................ 14107332.6

(51) Int. Cl.
     *A61B 5/024*        (2006.01)
     *A61B 5/00*         (2006.01)
     *A61B 5/1455*       (2006.01)

(52) U.S. Cl.
     CPC ...... *A61B 5/02416* (2013.01); *A61B 5/02433* (2013.01); *A61B 5/02438* (2013.01);
(Continued)

(58) Field of Classification Search
     CPC ... A61B 5/1455; A61B 5/00559; A61B 5/024; A61B 5/02416; A61B 5/14551;
(Continued)

(56) References Cited

U.S. PATENT DOCUMENTS 6,031,603 A     2/2000    Fine et al.
6,078,833 A     6/2000    Hueber
(Continued)

FOREIGN PATENT DOCUMENTS

CN        1148794 A     4/1997
CN        1187112 A     7/1998
(Continued)

OTHER PUBLICATIONS

Chinese Office Action, application No. 201480002601.4, dated May 28, 2019, 12 pages.
(Continued)

*Primary Examiner* — Eric F Winakur
(74) *Attorney, Agent, or Firm* — Ware, Fressola, Maguire & Barber LLP

(57) ABSTRACT

A device for monitoring heart rate or blood oxygen level during exercise is disclosed having sensors (106) and emitters (104), wherein the sensors (106) are used to monitor transmission from each of the emitters (104) in turn. This provides a possibility that a smaller device can be provided since less sensors and emitters can be used while obtaining more number of observations. In some embodiments the repeated use of sensors with different emitters introduces redundancy into the device so that the device is more robust and may function even in the event that one or two of the emitters and sensors have broken down.

8 Claims, 20 Drawing Sheets

(52) U.S. Cl.
CPC ...... *A61B 5/14551* (2013.01); *A61B 5/14552* (2013.01); *A61B 5/6817* (2013.01); *A61B 5/6824* (2013.01); *A61B 5/6826* (2013.01); *A61B 5/6833* (2013.01); *A61B 5/6847* (2013.01); *A61B 5/7214* (2013.01); *A61B 5/7221* (2013.01); *A61B 2505/09* (2013.01); *A61B 2560/0276* (2013.01); *A61B 2562/0238* (2013.01); *A61B 2562/043* (2013.01); *A61B 2562/164* (2013.01)

(58) Field of Classification Search
CPC ....... A61B 5/68; A61B 5/6801; A61B 5/6803; A61B 5/6813; A61B 5/6814; A61B 5/6815; A61B 5/6817; A61B 5/6824; A61B 5/6825; A61B 5/6826
See application file for complete search history.

(56) References Cited

U.S. PATENT DOCUMENTS

| | | | |
|---|---|---|---|
| 6,360,114 | B1 | 3/2002 | Diab et al. |
| 6,463,311 | B1 | 10/2002 | Diab |
| 6,553,242 | B1 | 4/2003 | Sarussi |
| 6,859,658 | B1 | 2/2005 | Krug |
| 6,931,268 | B1 | 8/2005 | Kiani-Azarbayjany et al. |
| 8,979,762 | B2 | 3/2015 | Ma et al. |
| 2006/0122520 | A1 | 6/2006 | Banet et al. |
| 2007/0060807 | A1 | 3/2007 | Oishi |
| 2009/0054751 | A1* | 2/2009 | Babashan ............ A61B 5/681 600/324 |
| 2012/0016245 | A1 | 1/2012 | Niwa et al. |
| 2012/0071768 | A1 | 3/2012 | Yamakoshi et al. |
| 2012/0190946 | A1 | 7/2012 | Bernreuter |
| 2014/0187885 | A1 | 7/2014 | Kreuzer |

FOREIGN PATENT DOCUMENTS

| | | |
|---|---|---|
| CN | 1326328 A | 12/2001 |
| CN | 1540314 A | 10/2004 |
| CN | 1919137 A | 2/2007 |
| CN | 201175331 Y | 1/2009 |
| CN | 201197707 Y | 2/2009 |
| CN | 101496717 A | 8/2009 |
| CN | 102355853 A | 2/2012 |
| CN | 202526183 U | 11/2012 |
| CN | 202960526 U | 6/2013 |
| CN | 103610467 A | 3/2014 |
| CN | 203564224 U | 4/2014 |
| CN | 103767696 A | 5/2014 |
| CN | 101953683 A | 12/2014 |
| EP | 0897692 | 2/1999 |
| EP | 0 957 747 B1 | 2/2004 |
| EP | 2 077 091 A3 | 10/2009 |
| EP | 2305104 | 4/2011 |
| WO | 95/26676 A1 | 10/1995 |
| WO | 96/41566 A2 | 12/1996 |
| WO | 2007/012931 A2 | 2/2007 |
| WO | 2012/135325 A2 | 10/2012 |

OTHER PUBLICATIONS

Bibliographic data including English abstract, Pub. No. CN1540314A published Oct. 27, 2004, application No. CN200310103053 filed Oct. 31, 2003, 1 page.
Bibliographic data including English abstract, Pub. No. CN101496717A published Aug. 5, 2009, application No. CN200810006882 filed Feb. 3, 2008, 1 page.
Bibliographic data including English abstract, Pub. No. CN201197707Y published Feb. 25, 2009, application No. CN200820004147 filed Feb. 3, 2008, 1 page.
English Abstract for CN103610467A, 2 pages.
English Abstract for CN201175331Y, 2 pages.
English Abstract (machine translation) for CN101953683A, 1 page.
English Abstract for CN202526183U, 2 pages.
Search Report for HK short-term patent application numbered HK1400233 filed Jul. 22, 2014, 9 pages total.
International Search Report, PCT/CN2014/082722, 3 pages.
English Abstract, CN202960526U, 2 pages.
English Abstract, CN203564224U, 2 pages.
English Abstract, CN103767696, 2 pages.
Alzahrani et al., A Multi-Channel Opto-Electronic Sensor to Accurately Monitor Heart Rate against Motion Artefact during Exercise, Sensors 2015, 15, 25681-25702 (22 pages total).
Mecnika et al., Wearable PPG Sensor Matrix for Cardiovascular Assessment, Material Science, Textile and Clothing Technology, Aug. 2013, pp. 76-82 (7 pages total).
Bibliographic data including English Abstract, Document CN000001540314A, DEPATISnet, 3 pages.
Chinese Office Action dated Oct. 30, 2023 for Application No. 202110389590.1, 6 pages.

\* cited by examiner

DEVICE AND METHOD SUITABLE FOR MONITORING ARTERIAL BLOOD IN A BODY PART

FIELD OF THE INVENTION

The current invention relates to a device suitable fear monitoring arterial blood in a body part. In particular, the current invention relates to a device suitable for monitoring arterial blood in a body part for determining heart rateor oxygen level daring exercise.

BACKGROUND OF THE INVENTION

A type of heart rate monitors measures heartbeat based on the absorption or transmission of infrared light projected through alimb or digit of a person, oranimal. The heart rate monitor typically comprises an emitter and a sensor. The emitter emits infrared light into the limb towards the sensor. Skin, tissues, venous blood and arterial blood absorb and reflect parts of this infrared light. However, the volume of arterial blood periodically increases and decreases with heartbeat. This causes the absorption and reflection of the infrared light to fluctuate with the heartbeat, which is detected by the sensors as periodic fluctuations of infrared transmission. This can be distinguished from the relatively constant effects of skin, tissue and venous blood on infrared light transmission.

There are generally two methods of measuring infrared light projected into a limb. In the first method, the emitter and the sensor are placed on somewhat opposite sides of the limb, while avoiding any bone within the limb, so that the infrared is transmitted from the miner to the sensor through the limb. In the other method, the emitter and the sensor are placed somewhat on the same side of the limb, so that a portion of the infrared light from the emitter projected into the limb is dispersed by the layers of tissues in the limb to arrive at the sensor.

Unfortunately, the accuracy of such heart rate monitors is affected by wearer's movements which introduce noise into the infrared transmission detected by the sensor. This is due in part to relative dislocation of the emitter and the sensor as the wearer moves, and in part to the flexing of the limb during movements which increase or decrease the transmission path length between the emitter and the sensor. That is, the skin and soft tissues of the limb is capable of wobbling and affecting the length of the transmission path.

A heart rate monitor in the form of an arm band arranged with three pairs of emitter and sensor has been proposed. The pairs are positioned on the arm band in such a way that noise caused by movements of the wearer of the arm band and detected by the three sensors are observed in different directions and angles, and are therefore mutually out-of-phase. In this way, the three pairs of emitter and sensor provide three sets of observations which can be used to remove noise components without requiring any external sensors to create a motion reference, as is required in many other earlier heart rate monitors of similar technology. However, this heart rate monitor requires three independent observations which have to be obtained by the same number of emitter and sensor pairs; a single pair of emitter and sensor is not enough for provide a sufficient number of independent observations. Unfortunately, the three emitter and sensor pairs compromise the robustness of the heart rate monitor, as the heart rate monitor will tail to work as soon as any one of the three sensors or three emitters fails to work. Also, manufacture and repair of this heart rate monitor is costly since so many emitters and sensors are required.

Accordingly, it is proposed to provide a heart rate monitor which is at least as accurate in determining heart rate with more robust resistance to malfunction, and preferably providing the possibility of using less hardware while achieving the same or better performance.

SUMMARY OF THE INVENTION

In a first aspect, the invention proposes a device suitable for monitoring arterial blood in a body part, the device being suitable for wearing on the body part, and the device comprising: a plurality of light emitters at least one sensor, the plurality of light emitters arranged such that light from the plurality of light emitters is capable of passing through the body part to arrive at the least one sensor, wherein: the plurality of light emitters emit light in consecutive order to be detected by the at least one sensor.

The device can be used as a heart rate monitor. Alternatively, the device can be used as part of an oximeter.

The invention provides an advantageous possibility that only one sensor is required to obtain a plurality of signal observations by detecting transmissions from different emitters. This reduces the number of sensors required to obtain an equal number of observations. This also reduces the amount of hardware and allows the device to be made smaller, lighter and cheaper.

In a certain embodiment, the at least one sensor is a plurality of sensors. The plurality of sensors and the plurality of emitters are capable of being defined as a plurality of sensor and emitter pairs, wherein the emitter in a first pair of sensor and emitter is capable of emitting to the sensors of at least two other pairs, and the sensor in the first pair is capable of detecting light from the emitter in each of the at least two other pairs.

Optionally, two sensors are used to obtain at least four observations of light transmissions or, as the ease may be, just three: observations may be selected for use out of the four observations. This allows that the number of sensors used is less than the equivalent number of observations obtainable, effectively reducing the amount of hardware required for obtaining that number of observations. As the skilled man knows, having a plurality of observations is useful for minimising noise to signal ratio.

More preferably, three sensors are used to obtain at least three observations of light transmissions. Typically, three sensors can be used with two emitters to provide six observations. Therefore, in the event that anyone of the three sensors fails to work, there will still be at least two sensors working with the two emitters to provide four observations. The four observations may all be used to monitor heart rate but it is possible, as a matter of choice, that only three out of the four observations may be used. In other words, if not more than three or four observations are required to produce a stable monitoring of heart rate, the use of three sensors with two emitters provides redundancy of three or two observations respectively without requiring additional hardware. This provides hack up or redundant observations in the event one of the sensors fails to work. In another situation, one emitter may fail to work but the device may still monitor heart rate based on three data observations obtained from the remaining three sensors and one emitter.

Monitoring heart rate based on four observations of data is already superior to most prior art devices, which typically use three observations only. Furthermore, the prior art provides that each sensor is dedicated to only one emitter and three sensor and emitter pairs are used to provide only three of the number of observations is the same as the number of sensors. In other words, there is no redundancy of observations in such prior art.

In one embodiment, the device is a circular support capable of being attached to the body part, the at least one sensor is a plurality of sensors, the plurality of sensors being evenly distributed about the circular support. This avoids exposing all the plurality of sensors to ambient light from any one direction at the same time; the distribution about a circular support prevents strong ambient light coming from one direction and striking on a sensor from striking the other sensors too. Coupled with the advantage of redundant observations, particularly where the device comprises at least three sensors coupled with at least two emitters taking turns to emit light, this provides the possibility that the device is able to monitor heart rate with sufficient number of data observations even when the ambient light has crippled one of the sensors. The capacity to avoid breakdown when one of the sensors fail to work provides a possible advantage of lowering hardware cost by reducing the light detection range required for each sensor. Preferably, the circular support is in the form of a ring wearable on finger.

In a more specific preferred embodiment, the device comprises three of the at least one sensor are arranged to detect light transmission from three light emitters, each of the three sensors is arranged to detect light transmission from at least two of the light emitters so as to detect at least six observations of light transmissions by the three sensors, the device comprises a support capable of being attached to the body part, the support having a curved surface, the plurality of sensors is distributed along the curvature of the curved surface of the support so its to reduce the likelihood of uniform exposure of the plurality of sensors to ambient light from any one direction at the same time, the device is configured to monitor arterial blood in a body part using only four observations such that two of the at least six observations are redundant observations, and the device is configured to disregard the two observations of any of the sensors which the device detects as failing to work properly due to saturation by ambient light while regarding the four observations of the remaining working sensors to monitor arterial blood.

Preferably, the plurality of sensors is arranged in mutually different positions. Optionally, different positions refers to different mutual distances from the at least one light emitter. Alternatively, different positions refers to different directions to the at least one light emitter. Having different directions or distances promotes diversity in noise data, increasing the likelihood that noise sensed by each sensor is different from or is out of phase with those detected by the other sensors. This allows noise to be eliminated more easily. In contrast, heartbeat signals detectable by all the sensors are synchronous and in-phase, and may be extracted from the noise.

In a second aspect, the invention proposes a method of obtaining observations of light transmission to monitor arterial blood in a body part, comprising the steps of: providing at least one sensor at a side of the body part; providing a first emitter and second emitter at different sides of the body part such that light emitted from the first emitter and second emitter transmits through the body part to arrive at the at least one sensor; causing the first emitter and second emitter to emit light one after the other, and the at least one sensor to detect light from the first emitter and second emitter in accordance to the order in which the first emitter and second emitter emit light to obtain a first observation and a second observation.

Preferably, the method comprises the further steps providing a further sensor at a further side of the body part; and causing the further sensor to detect light from either the first emitter or the second emitter to obtain a third observation. Preferably, the method also comprises the further step of: causing the further sensor to detect light from either the first emitter or the second emitter to obtain a fourth observation.

Preferably, the method comprises the further steps of: determining any one of the sensors or emitters as failing to work properly; disregarding the observations made with the one of the sensors or emitters failing to work properly and regarding the readings of the remaining working sensors to monitor arterial blood. Typically, the sensor fails to work properly due to saturation by over exposure to ambient light.

The ability to disregard any of the sensor or emitter which fails to work properly provides the device with adaptability to different ambient conditions.

BRIEF DESCRIPTION OF THE DRAWINGS

It will be convenient to further describe the present invention with respect to the accompanying drawings that illustrate possible arrangements of the invention, in which like integers refer to like parts. Other embodiments of the invention are possible, and consequently the particularity of the accompanying drawings is not to be understood as superseding the generality of the preceding description of the invention.

DESCRIPTION OF EXEMPLARY EMBODIMENTS

Figure 1:
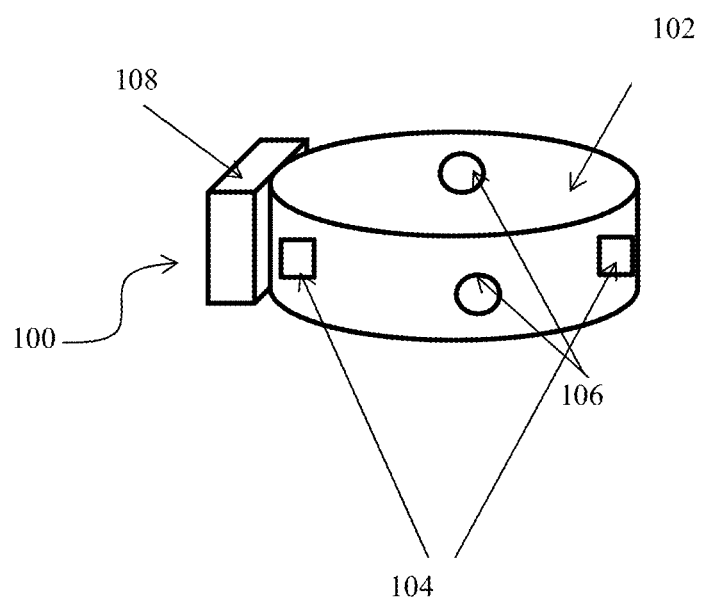
FIG. 1 is an illustration of a first embodiment of the invention.

FIG. 1 shows a first embodiment 100, comprising a ring 102 which is a heart rate monitor. The ring can be worn on the finger of a person whose heart rate is to be monitored during exercise. The finger is not illustrated in the drawing.

The ring 102 is installed with two emitter-and-sensor 106 pairs. Therefore, there are two emitters 104 and two sensors 106 in total. A suitable housing 108 is attached to the ring 102 for containing a microprocessor and memory required for operating the emitters 104 and sensors 106, and for manipulating infrared signal data as detected by the sensors 106.

Typically, the emitters 104 are Light Emitting Diodes or LEDs which emit light that is absorbable by blood, such as infrared. In other embodiments however, any other suitable frequency can be used including visible red, green or blue light, or any combination thereof.

The two emitters 104 are provided in the ring 102 such that they are at opposite sides of the wearer's finger when the ring 102 is worn. The two sensors 106 are also provided such that they are at opposite sides of the finger when the ring is worn but also to be at about 90 degrees to an imaginary line drawn through the emitters 104. The positions of both sensors 106 allows each sensor 106 to be capable of detecting light projected into the finger by both emitters 104.

Figure 2:
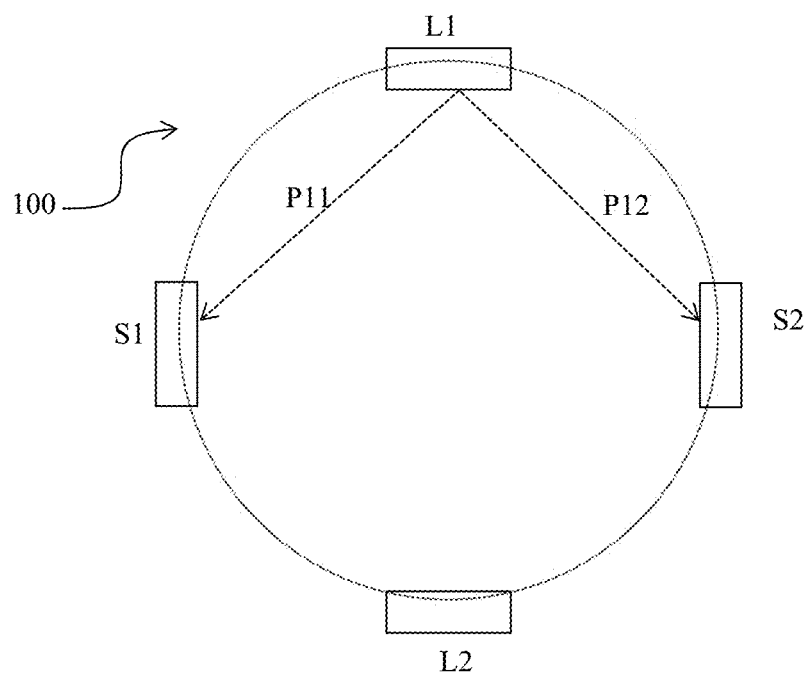
FIG. 2 is a schematic diagram of the internal arrangement of the embodiment of FIG. 1.

FIG. 2 is a schematic diagram of the arrangement of the two emitters 104 and two sensors 106 in the ring 102. Due to the small radius of the ring 102, light emitted by the emitters 104 need not be projected directly at the sensors 106. Instead, the sensors 106 merely needs to detect infrared light scattered through or reflected by tissues and blood in the finger. Other ways of arranging the emitters 104 and the sensors 106 are possible as long as each emitter 104 is placed a distance away from both of the sensors 106, such that a sufficiently long transmission path through the finger is provided for absorption of infrared light by arterial blood.

The microprocessor operates the emitters 104 such that they emit infrared light one after the other. Thus, both sensors 106 first detect infrared light scattered through the finger from one emitter 104 and then detect infrared light scattered through the finger from the other emitter 104.

Figure 3:
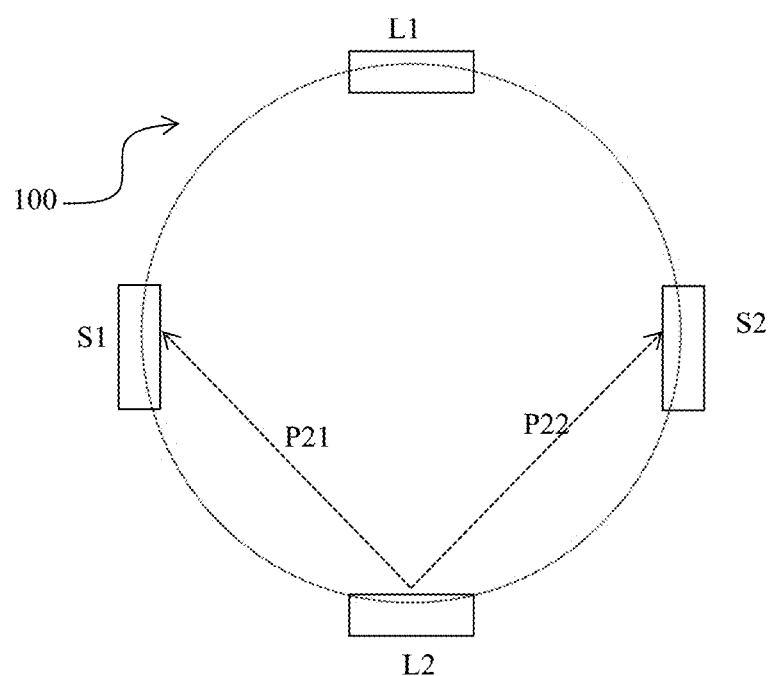
FIG. 3 is a schematic diagram of the internal arrangement of the embodiment of FIG. 1.

As illustrated in FIG. 2 and FIG. 3, transmission paths P11 and P12 are observed by sensors S1 and S2 respectively when emitter L1 emits infrared light into the finger. The infrared signals observed by both sensors S1 and S2 are then recorded for processing by the microprocessor. Subsequently, the microprocessor instructs emitter L1 to stop emitting infrared light and instructs emitter L2 to start emitting infrared light. Both sensors S1 and S2 then detect the infrared signals via transmission paths P21 and P22, respectively.

Accordingly, four transmission paths through the finger P11, P12, P21, P22 are monitored in this embodiment. Four sets of data are observed using only two sensors 106 and two emitters 104. In contrast, the prior art requires three emitters and three sensors to obtain just three observations. Advantageously, the present embodiment requires less hardware while making a greater number of observations than devices of the prior art.

Typically, the sensors can detect fluctuating infrared transmissions through the finger which are attributed to heartbeat. Skin, tissue, venous blood, and the arterial blood are all capable of absorbing infrared light. However the volume of arteries periodically increases and decreases with the pumping of the heart, giving rise to these fluctuating transmissions.

Figure 4:
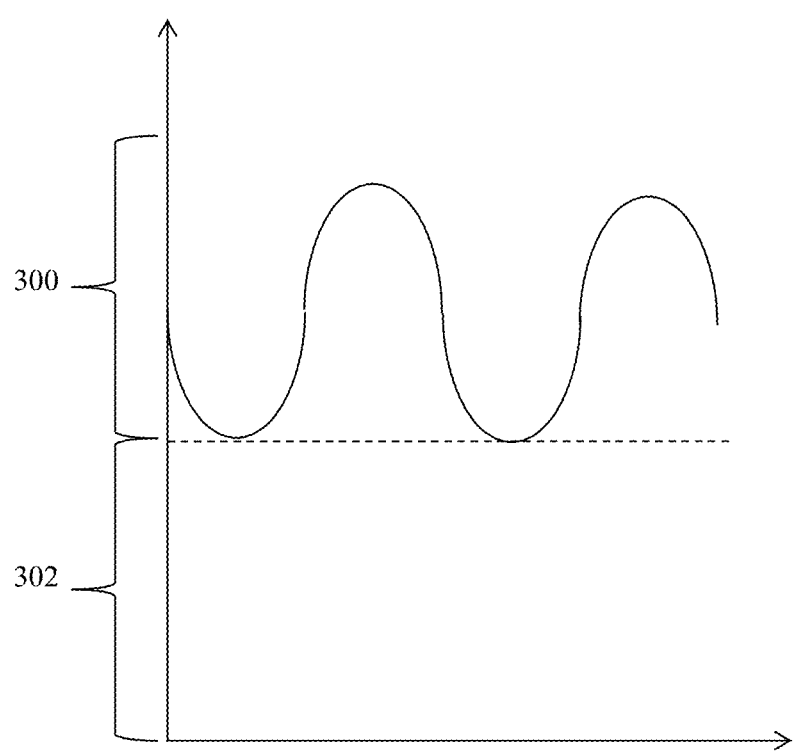
FIG. 4 is a chart showing noise signals which can be treated by the embodiment of FIG. 1.

FIG. 4 explains how these fluctuating transmissions come about. The vertical axis of the chart in FIG. 4 shows absorption of the infrared light. Together, the troughs form the base 302 of the waveform which is indicative of the amount of light absorbed by skin, tissues, venous blood, which are relatively constant, and when artery blood volume is smallest. The magnitude 300 between the troughs to the peaks is attributed to an increase of infrared absorption when the artery volume increases and is filled with blood.

However, the infrared transmission signals detected by the sensor are subjected to noise when the wearer exercises. For example, the wearer's movements can cause continual small physical displacements of emitter and sensor positions. Furthermore, the cross-sectional area of the finger on which the ring is worn varies easily when the finger is flexed during exercise. All these movements vary the distance of the transmission paths through the finger, which introduce variations into the transmission signals as unwanted noise.

Figure 5:
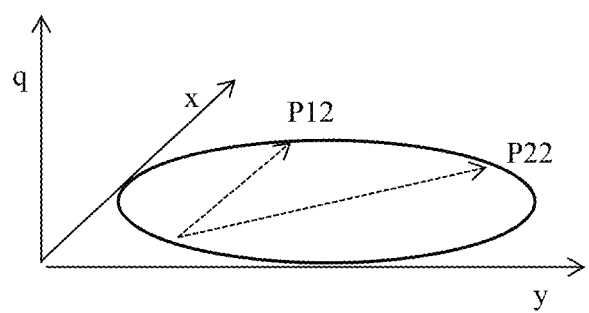
FIG. 5 is a diagram explaining the effects of noise components which can be treated by the embodiment of FIG. 1.

In practice, only transmission path changes in the plane defined by the sensors 106 contribute noise. FIG. 5 illustrates the plane as an x-y plane. Muscle or tissue volume changes in the q-axis perpendicular to the x-y plane are relevant only if they cause the finger to expand or contract in the x-y plane, or if any vertical movements cause the ring 102 to slip along the finger which effectively moves the x-y plane along the finger length.

Figure 6:
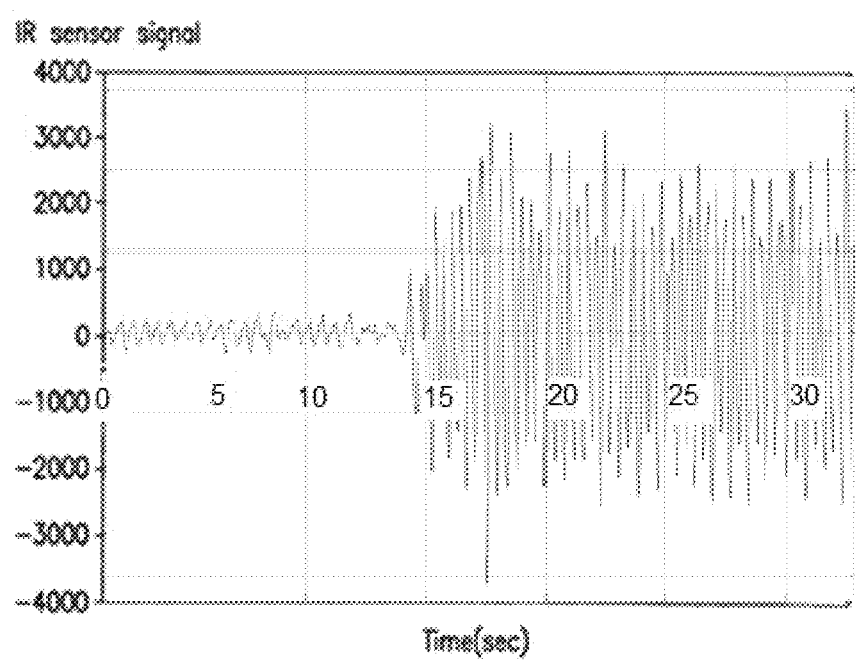
FIG. 6 is a chart showing; heart rate and noise motions which can be treated by the embodiment of FIG. 1.

FIG. 6 is a chart showing bow the heart rate of a wearer is detected as a periodic signal and how the periodic heart rate signal can be overwhelmed by noise due to movements of the wearer. In about the first 10 seconds of the chart the wearer stays stationary and the signals representing heart rate are low in peak-to-peak amplitude because volumetric changes in the arteries tend to be relatively small. All periodic fluctuations in the infrared transmission signal can be attributed to arterial pulsation, and one set of observation obtained using one emitter and one sensor may even be enough to monitor the heart rate. The DC component in these 10 seconds is largely contributed by tissues, venous blood and other stable components in the wearer's finger, while the AC component is contributed by heartbeat.

At 15 seconds in the chart, however, when the wearer starts to run, jump and or move his finger, the movements easily overshadow the heart rate signals with noise. That is, the AC component now include noise and fluctuates much higher and lower about the DC level and overshadows the AC component contributed by the heartbeat.

The amount of light emitted by one of the emitters 104 and detected at any one of the sensors 106 can be approximately modelled as follows:

$$m(t)=LI_0(t)(1+\gamma hb(t))(1+N_s(t)+N_f(t)+z(t))$$

where:
   m(t) is the signal received at any one of the IR sensors 106
   L is constant gain of the IR sensor
   $I_0(t)$ is the transmitted signal to the IR emitter
   hb(t) is the heart rate signal
   γ is coupling coefficients of the heart rate signal hb(t)
   $N_s(t)$ is slow varying noise in the detected signals
   $N_f(t)$ is are typical additive thermal noise in the detected signals, and
   z(t) is noise signals due to movement caused by flexing of the body part.

If $N_s(t)=0$, $N_f(t)=0$, z(t)=0, the infrared signals are proportional to periodic pumping of arterial blood by the heart, i.e.

$$m(t)=LI_0(t)(1+\gamma hb(t))$$

If there is no noise in the infrared signals, the peaks in the waveform can be directly counted to obtain the heart rate of the wearer. However, if there is a lot of noise from wearer movement and z(t) becomes significant, then the infrared signals have to be mathematically treated to extract the heart rate signal from the noisy signal.

Figure 7:
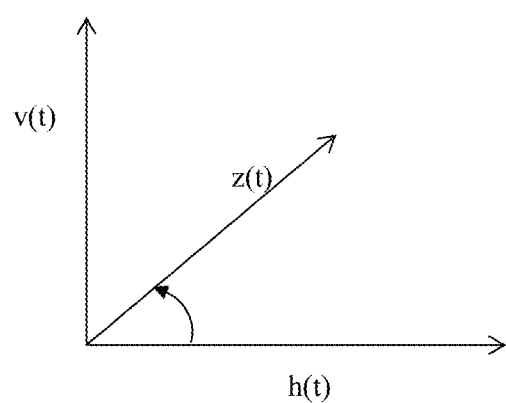
FIG. 7 further explains the noise component discussed for FIG. 5.

FIG. 7 illustrates how movement signals z(t) in the x-y plane defined by the location of the sensors 106 can be re-written as:

$$z(t)=\varepsilon[h(t)\cos(\theta)+v(t)\sin(\theta)]$$

where
- $h(t)$ is the movement signal caused by flexing the finger in the wearer's horizontal direction;
- $v(t)$ is movement signal caused b flexing the finger in the wearer's relative vertical direction;
- the direction of sensor k is $\theta$ from the horizontal direction; and
- $\varepsilon$ is the coupling coefficient for the movement signal to the sensor.

Movements affecting the infrared signals are mathematically determined for their effects within the x-y plane only. The x-y plane is defined by the sensors 106 and need not necessarily be 'horizontal' or parallel to the ground.

In this embodiment, the four observations obtained from the two sensors 106 can be modelled as follows:

$$m_1(t)=L_1 I_{01}(t)(1+\gamma_1 hb(t))(1+N_{s1}(t)+N_{f1}(t)+z_1(t)) \quad (1)$$

$$m_2(t)=L_2 I_{02}(t)(1+\gamma_2 hb(t))(1+N_{s2}(t)+N_{f2}(t)+z_2(t)) \quad (2)$$

$$m_3(t)=L_3 I_{03}(t)(1+\gamma_3 hb(t))(1+N_{s3}(t)+N_{f3}(t)+z_3(t)) \quad (3)$$

$$m_4(t)=L_4 I_{04}(t)(1+\gamma_4 hb(t))(1+N_{s4}(t)+N_{f4}(t)+z_4(t)) \quad (4)$$

Where:
- $m(t)$, $m_2(t)$, $m_3(t)$, $m_4(t)$ are the signal received at the 4 sensors 106 respectively
- $L_1$, $L_2$, $L_3$, $L_4$ are constant gain of each IR sensors 106
- $I_{01}(t)$, $I_{02}(t)$, $I_{03}(t)$, $I_{04}(t)$ are the transmitted signal to the IR LED emitters 104 respectively
- $hb(t)$ is the heart rate signal
- $\gamma_1$, $\gamma_2$, $\gamma_3$, $\gamma_4$ are coupling coefficients of the heart rate signal $hb(t)$
- $N_{s1}(t)$, $N_{s2}(t)$, $N_{s3}(t)$, $n_{s4}(t)$ are slow varying noise in the detected signals
- $N_{f1}(t)$, $N_{f2}(t)$, $N_{f3}(t)$, $N_{f4}(t)$ are typical additive thermal noise in the detected signals, and
- $z_1(t)$, $z_2(t)$, $z_3(t)$, $z_4(t)$ are noise signals due to movement.

The movement noise signals $z_1(t)$, $z_2(t)$, $z_3(t)$, $z_4(t)$ can be re-written as:

$$z_k(t)=\varepsilon_k(h(t)\cos(\theta_k)+v(t)\sin(\theta_k))$$

where
- $h(t)$ is the movement signal in the horizontal;
- $v(t)$ is movement signal in the relative vertical direction;
- the direction of sensor 106 k is $\theta_k$ from the horizontal direction; and
- $\varepsilon_k$ are coupling coefficients for the movement signal to the sensor 106.

Assuming that both $\gamma_k$, $\varepsilon_k$ are much smaller than 1, the infrared signals at each sensor can be represented as being composed of both DC and AC components, ($m_{ack}(t)$, $m_{dck}(t)$).

When the wearer first puts on the ring 102, he is requested by the microprocessor via a display (not shown) in the housing 108 to stay stationary without moving. At this stage, the infrared signals detected by the sensors 106 can be attributed to heart rate only. The raw data from each of the sensors 106 is firstly treated with a simple Finite Input Response (FIR) low pass filter to remove all high frequency signals. Subsequently, the slow drifting DC offset is removed using a filter or a moving window to extract the DC offset and subtract it from the signals. At this stage, if the microprocessor detects that the infrared signals read by the different sensors 106 differ greatly in amplitude, the gain of each of the four sensors 106 is adjusted until the difference in the amplitudes of the transmission signals fall within a pre-determined deviation. By this, the gain of each of the sensors are normalised, and equations (1) to (4) can then be approximated as:

$$m_{ac1}(t)=hb(t)+N'_{s1}(t)+N'_{f1}(t)+z_1'(t) \quad (1b)$$

$$m_{ac2}(t)=hb(t)+N'_{s2}(t)+N'_{f2}(t)+z_2'(t) \quad (2b)$$

$$m_{ac3}(t)=hb(t)+N'_{s3}(t)+N'_{f3}(t)+z_3'(t) \quad (3b)$$

$$m_{ac4}(t)=hb(t)+N'_{s4}(t)+N'_{f4}(t)+z_4'(t) \quad (4b)$$

where $N'_{sk}(t)$, $N'_{fk}(t)$, $z_k'(t)$ are scaled versions of the original noise signals.

After normalisation, the ring 102 can now be used to monitor heart rate. When there is no movement or a very small amount of movements, the deviation of the amplitudes of signals detected by the sensors remains at the normalised level. The maximum signal to noise ratio (SNR) of the heart rate signal can be obtained by adding up the normalised AC component input signal, i.e.

$$y(t)=m_{ac1}(t)+m_{ac2}(t)+m_{ac3}(t)+m_{ac4}(t)$$

Effectively, the noise will be reduced as the signal is accentuated by the summation of the independent observations of each sensor.

However, when the wearer exercises, noise signals $z_1'(t)$, $z_2'(t)$, $z_3'(t)$, $z_4'(t)$ dominate the signals detected by the sensors 106. The noise can then be treated by finding the column vector $\hat{w}=[w_1\ w_2\ w_3\ w_4]^T$ where $$\hat{y}=\hat{w}^T M$$

; and $$M = \begin{bmatrix} m_{ac1}[0]m_{ac1}[1] & \ldots & \ldots & m_{ac1}[K-1] \\ m_{ac2}[0]m_{ac2}[1] & \ldots & \ldots & m_{ac2}[K-1] \\ m_{ac3}[0]m_{ac3}[1] & \ldots & \ldots & m_{ac3}[K-1] \\ m_{ac4}[0]m_{ac4}[1] & \ldots & \ldots & m_{ac4}[K-1] \end{bmatrix};$$

and $$\hat{y}=[y[0]y[1]\ \ldots\ y[K-1]]$$

and $\hat{y}$ is a linear combination of input signal which maximizes:

$$\frac{\hat{w}^T \hat{s}\hat{s}^T \hat{w}}{\hat{w}^T \mathfrak{R}_{mm} \hat{w}}$$

where
- $\mathfrak{R}_{mm}$ is the cross correlation matrix of the 4 signals from movement.
- $\hat{s}=[s_1\ s_2\ s_3\ s_4]^T$ is the corresponding gain of the heart rate signal, in this case when all the 4 input channels are normalized
- $\hat{s}=[1\ 1\ 1\ 1]^T$ and $\mathfrak{R}_{mm}=MM^T-\sigma^2 \hat{s}\hat{s}^T$, where $\sigma^2$ is the variance of the heart rate signal. As $\mathfrak{R}_{mm}$ is positively defined, it can be written that $$\mathfrak{R}_{mm} R^{1/z}, R^{1/z}$$

and it can be written that $$\hat{u} = R^{1/z}\hat{w}$$

and $$\hat{w} = R^{-1/z}\hat{u}$$

Accordingly, the problem to be solved becomes:

$$\max_{\|\hat{u}\|} \hat{u}^T R^{-\frac{1}{2}} \hat{s} \cdot \hat{s}^T R^{-\frac{1}{2}} \hat{u}$$

or $$\max_{\|\hat{u}\|} \left( \hat{u}^T R^{-\frac{1}{2}} \hat{s} \right)^2$$

The expression is maximum when:

$$\hat{u} = R^{-1/2} \hat{s}$$

$$\therefore \hat{w} = R^{-1/2}(R^{-1/2}\hat{s}) = \mathfrak{R}_{mm}^{-1} \hat{s}$$

where $\mathfrak{R}_{mm} = MM^T - \sigma^2 \hat{s}\hat{s}^T$

To remove movement noise, the four sets of observations obtained from the two sensors 106 are used. If the four signals detected in the four transmission paths are synchronous and in-phase, and if the amplitudes of all the four signals differ only within a signal standard deviation of σ, it may be taken that heartbeat signals dominate the infrared signals with little noise. The signals can simply be added up and the peaks in the signal waveform counted to determine heart rate.

On the other hand, if noise dominates the infrared signals, the infrared signals will not be in phase and the amplitudes of all the four signals will differ beyond the standard deviation σ. In this case, to extract the heart rate signal, the correlation index across the four signals is calculated. That is, the covariance matrix of the signals calculated:

$$\mathfrak{R}_{mm} = MM^T - MM^T - \sigma^2 \hat{s}\hat{s}^T.$$

As mentioned earlier $\sigma^2 \hat{s}\hat{s}^T$ was obtained by calculating the standard deviation of the four input signals when there was no wearer movement. The four input signals are then normalised to standard deviations of and σ, and $\sigma^2 \hat{s}\hat{s}^T$ becomes $$\sigma 2 = \begin{bmatrix} 1 & 1 & 1 & 1 \\ 1 & 1 & 1 & 1 \\ 1 & 1 & 1 & 1 \\ 1 & 1 & 1 & 1 \end{bmatrix}$$

The vector can be calculated, where $$w = \mathfrak{R}^{-1} \hat{s}$$

where w is a 4×1 column vector: $\hat{y} = \hat{w}^T M$
y[n] is a linear combination of the 4 input signals
At $\hat{s} = [1\ 1\ 1\ 1]^T$ all four channels would be normalized.

The above mathematical treatment normalises the signals received by the sensor such that the combined signals have the lowest total energy. Having the lowest total energy implies that the total amount of noise has been adjusted to be at the lowest and least influential.

Furthermore, the independent observations of transmission signals due to heartbeat will be in phase with each other, differing only by a scaling factor. Therefore, if the infrared signals are summed up with some specific weight, the noise signals can be minimized and hence increasing the signal to noise ratio.

Typically, the wearer's movements can be quite periodic when he is performing a repetitive exercise such as running. Nevertheless, these periodic exercise movements do not impart an identical and periodic noise to the sensor readings. This is because the several transmission paths through the linger between each pair of emitter and sensor are different, and it may be expected that unique noise is imposed on each sensor by the different local layers of wobbly tissue and other bodily components, even if the wearer's movements is periodic and applied to the device 100 as a whole. Accordingly, summation of the infrared signals detected by the different sensors will not add up to accentuate any identical periodic noise signals.

Figure 8:
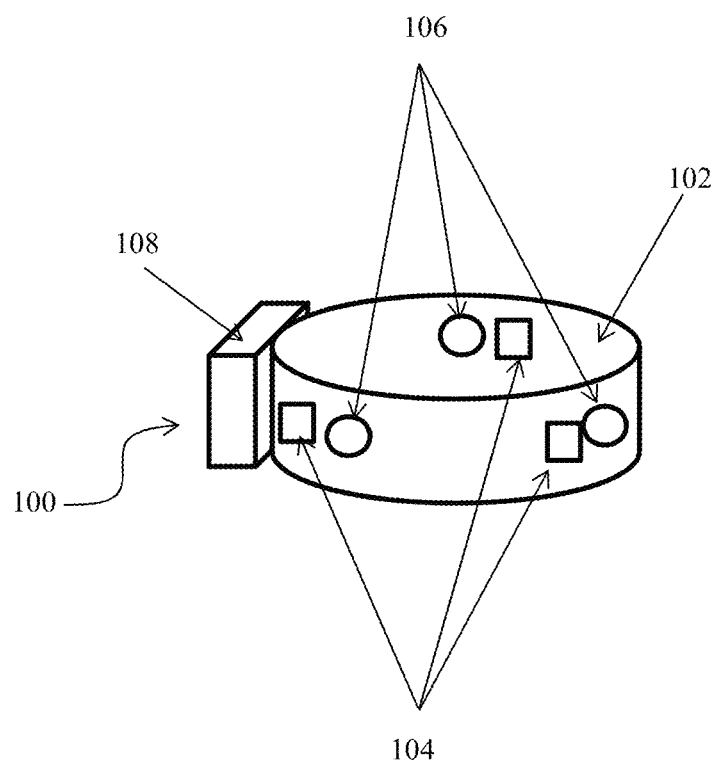
FIG. 8 shows a second embodiment to the invention.
Figure 9:
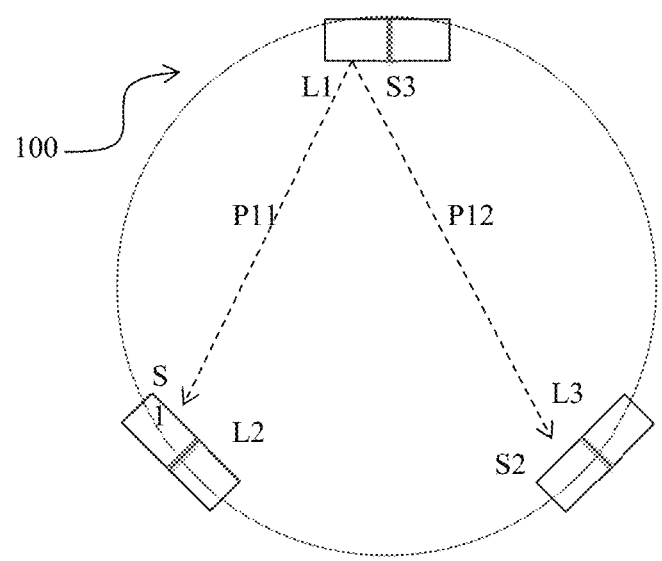
FIG. 9 further shows the second embodiment of FIG. 8.
Figure 10:
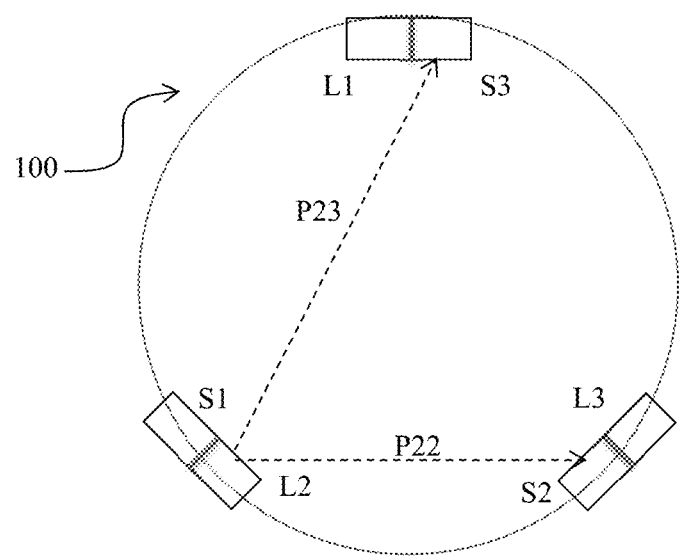
FIG. 10 further shows the second embodiment of FIG. 8.
Figure 11:
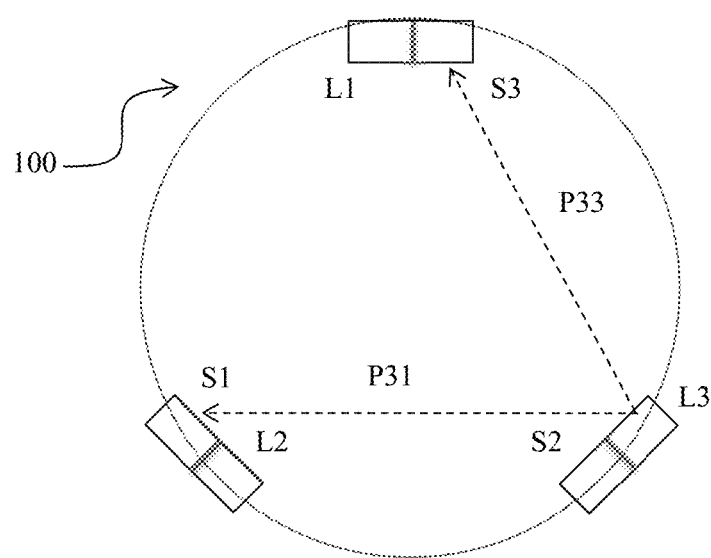
FIG. 11 further shows the second embodiment of FIG. 8.

To further improve signal to noise ratio, it is desirable to have more independent observations to increase observation diversity. FIG. 8 shows a second embodiment to this effect. FIG. 9 to FIG. 11 are schematics diagrams of the second embodiment of FIG. 8. The second embodiment comprises a ring 102 installed with three emitter-and-sensor pairs, instead of two. Each emitter 104 is placed immediately next to one of the sensors 106 and away from the other two sensors 106. In this way, each emitter 104 is able to project light to the two sensors 106 across the ring 102 and through the finger. Likewise, the sensor 106 immediately next to an emitter 104 is able to receive light from the two emitters 104 across the ring 102.

In operation, the emitters L1, L2, L3 are switched on in consecutive order, one after another. When emitter L1 is ON, both sensors S1 and S2 detect light from emitter L1 in respective transmission paths P11 and P12. When L2 is ON, sensors S2 and S3 detect light from emitter L2 in respective transmission paths P22 and P23. When L3 is ON, sensors S1 and S3 detect light from emitter L2 in respective transmission paths P31 and P33.

As with the first embodiment, in order to remove noise from wearer movements, the amplitudes of the six observations are normalized by calculating their variance or standard deviation. The detected signals are modelled as follows:

$$m_1(t) = L_1 I_{01}(t)(1+\gamma_1 hb(t))(1+N_{s1}(t)+N_{f1}(t)+z_1(t)) \quad (1a)$$

$$m_2(t) = L_2 I_{02}(t)(1+\gamma_2 hb(t))(1+N_{s2}(t)+N_{f2}(t)+z_2(t)) \quad (2a)$$

$$m_3(t) = L_3 I_{03}(t)(1+\gamma_3 hb(t))(1+N_{s3}(t)+N_{f3}(t)+z_3(t)) \quad (3a)$$

$$m_4(t) = L_4 I_{04}(t)(1+\gamma_4 hb(t))(1+N_{s4}(t)+N_{f4}(t)+z_4(t)) \quad (4a)$$

$$m_5(t) = L_5 I_{05}(t)(1+\gamma_5 hb(t))(1+N_{s5}(t)+N_{f5}(t)+z_5(t)) \quad (5a)$$

$$m_6(t) = L_6 I_{06}(t)(1+\gamma_6 hb(t))(1+N_{s6}(t)+N_{f6}(t)+z_6(t)) \quad (6a)$$

Where:
$m(t)$, $m_2(t)$, $m_3(t)$, $m_4(t)$, $m_5(t)$, $m_6(t)$ are the signal received at the 6 sensors 106 respectively
$I_{01}(t)$, $I_{02}(t)$, $I_{03}(t)$, $I_{04}(t)$, $I_{05}(t)$, $I_{06}(t)$ are the transmitted signal to the IR LED emitters 104 respectively
$L_1$, $L_2$, $L_3$, $L_4$, $L_5$, $L_6$ are constant gain of each IR sensors 106 hb(t) is the heart rate signal
$\gamma_1$, $\gamma_2$, $\gamma_3$, $\gamma_4$, $\gamma_5$, $\gamma_6$ are coupling coefficients of the heart rate signal hb(t)
$N_{s1}$, (t), $N_{s2}(t)$, $N_{s3}(t)$, $N_{s4}(t)$, $N_{s5}(t)$, $N_{s6}(t)$ are slow varying noise in the detected signals
$N_{f1}(t)$, $N_{f2}(t)$, $N_{f3}(t)$, $N_{f4}(t)$, $N_{f5}(t)$, $N_{f6}(t)$ are typical additive thermal noise in the detected signals, and $z_1(t)$, $z_2(t)$, $z_3(t)$, $z_4(t)$, $z_5(t)$, $z_6(t)$ are noise signals due to movement.

The subsequent mathematical treatment for six sensors 106 is the same as that described for the first embodiment.

Figure 12:
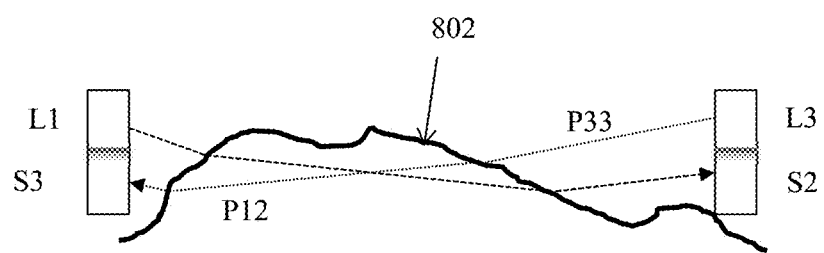
FIG. 12 explains the workings of the embodiment of FIG. 8.

FIG. 12 shows why although transmission paths P12 and P33 are practically the same physical path but the noise imposed onto the signals transmitted in paths P12 and P33 are not identical. This is because P12 and P33 are transmissions in opposite directions although the transmission transmits in virtually the same path 802 between the two sensor S2 and sensor S3. The random folds of skin on the finger and the different tissues under the skin provide an asymmetrical transmission path between sensor S2 and sensor S3. Therefore, the angle of infrared light incident on the skin from emitter L1 towards S2 is likely to be different from the angle of infrared light incident on the skin from emitter L3 towards S3. Similarly, the extent of reflection and penetration of the incident infrared light into the skin surface is different in the two different directions, as indicated by the arrows in FIG. 12. Thus, noise signals imposed on the sensors S2 and S3 due to movement and flexing of the finger are not identical in the different transmission directions. This explains why using the same physical transmission path for two sensors in different directions does not amount to replicating a same signal. This also explains why the wearer's periodic exercise movements do not impose periodic and identical noise signals on all the sensors even if wearer movements are periodic, as the different transmission directions ensures that the noise is unique in each sensor.

In both embodiments, the use of one sensor 106 with two different emitters 104 increases the number of independent observations made with each sensor. In the first embodiment, only two emitters 104 and two sensors 106 are required for obtaining four observations. In the second embodiment, three sensors 106 and three emitters 104 provide six observations. This is advantageous over the prior art as less sensors or emitters is required for obtaining a greater number of observations.

Figure 13:
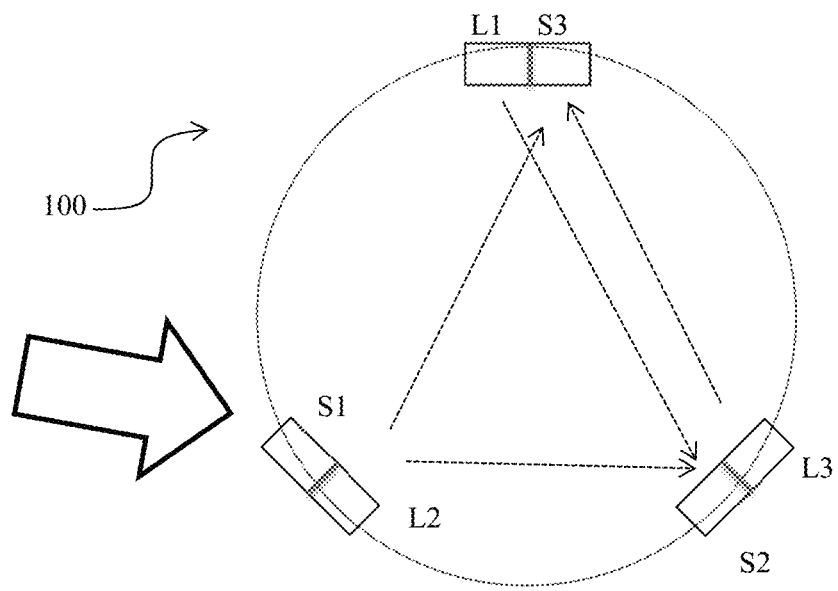
FIG. 13 explains an advantage in the embodiment of FIG. 8.

More advantageously, in the second embodiment, any one of the emitters 104 or the sensors 106 may break down and four observations are nevertheless obtainable. For example, temporarily failure situations may happen when ambient light shines directly into one of the sensors, saturating the sensor 106. FIG. 13 shows the ring of the second embodiment having three sensor and emitter pairs. Strong ambient light represented by the block arrow shines onto sensor S1 but is blocked by the wearer's finger over which the ring is worn from shining onto S2 and S3. When the sensor S1 is so exposed to ambient light, sensor S1 becomes saturated and unusable for detecting infrared transmission signals. However, as sensors S3 and S2 are blocked from the ambient light, sensors S3 and S2 remain functional.

Thus, sensor S3 remains capable of reading infrared transmission signals from L2 and L3, and sensor S2 remains capable of reading infrared transmission signals from L1 and L2. The microprocessor can detect that sensor S1 is saturated and disregard the sensor S1, and use the remaining four observations provided by sensors S2 and S3 to determine the heart rate. As described, L1 and L2 takes turns to emit to the sensors S2 and S3 to provide the four observations. In contrast, an ambient light saturation of a sensor in a prior art device which uses three sensors to detect light from three respective, separate emitters will compromise the accuracy of the device because one observation becomes unusable.

As a matter of choice, in the first embodiment, only three observations may be used to monitor heart rate from the two emitters 104 and two sensors 106, even though four observations are obtainable. Similarly, in the second embodiment, only three observations may be used even though the three sensors 106 and three emitters 104 provide the possibility of six observations, particularly where any two of such three observations is obtained using the same sensor 106.

Accordingly, the embodiments described includes a device suitable for monitoring arterial blood in a body part 100 comprising: a plurality of light emitters 104 at least one sensor 106, the plurality of light emitters 104 arranged such that light from the plurality of light emitters 104 is capable of passing through a body part to arrive at the least one sensor 106, wherein: the plurality of light emitters 104 emits light in consecutive order to be detected by the at least one sensor 106. The device for monitoring arterial blood 100 has been described as a heart rate monitor.

Furthermore, the embodiments described includes a device suitable for monitoring arterial blood in a body part 100 comprising at least one light emitter 104, a plurality of sensors 106, the at least one light emitter 104 arranged such that light from the at least one light emitter 104 is capable of passing through the body pan to arrive at the plurality of sensors 106.

Furthermore, the embodiments described includes a method of obtaining observations of light transmission to monitor heart rate comprising the steps of: providing at least two sensors 106 for detecting light, placing the two sensors 106 at different sides of a body part, providing a first light emitter 104 at another side of the body part, such that light emitted from emitter 104 transmits through the body part to arrive at the at least two sensors 106, the transmission path to one of the sensors 106 providing a first observation, anal the transmission path to the other of the sensors 106 providing a second observation.

Furthermore, the embodiments described includes a method of obtaining observations of light transmission to monitor heart rate comprising the steps of: providing at least two light emitters 104, providing a sensor 106 for detecting light, placing the at least two emitters 104 at different positions on a side of the body part, providing the sensor 104 on another side of the body part, such that light emitted from the emitters 104 is capable of transmitting through the body part to arrive at the sensor 106, and operating the emitters 104 one after another to obtain different observations at the sensor 106.

While there has been described in the foregoing description preferred embodiments of the present invention, it will be understood by those skilled in the technology concerned that many variations or modifications in details of design, construction or operation may be made without departing from the scope of the present invention as claimed.

For example, although the sensors 106 have been described to detect light from the emitters 101 transmitted through the body part, it is possible that the sensors 106 can be arranged in other embodiment to detect light from the emitters 104 by reflection or dispersion from the body part. In this case, the sensors 106 would be placed next to but a distance away from the emitters 104.

Figure 14:
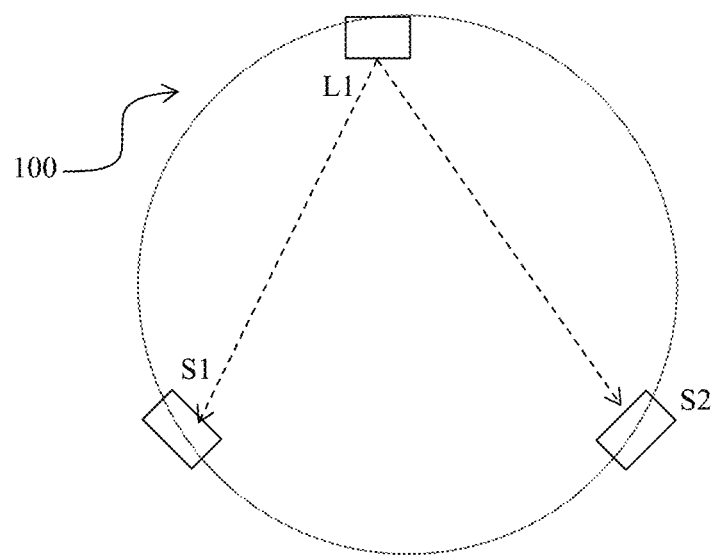
FIG. 14 shows yet a further embodiment of the invention.

FIG. 14 shows a further embodiment which is much simpler, comprising only one emitter 104 placed on one side and two sensors 106 placed at different angles on another side of the body part across from the emitter. Only two observations can be made from the two sensors. This embodiment can be used in situations where noise from movements is very unlikely, such for monitoring the heart rate of an infant, but use of only two sensors and one emitter instead of two sensors and two emitters allow a much lighter, smaller and cheaper device 100.

Figure 15:
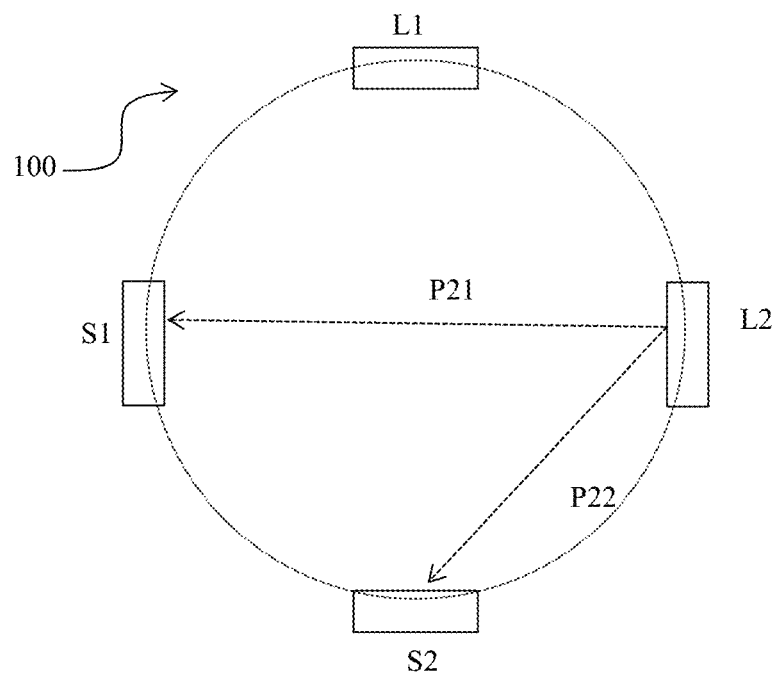
FIG. 15 shows yet a further embodiment of the invention.
Figure 16:
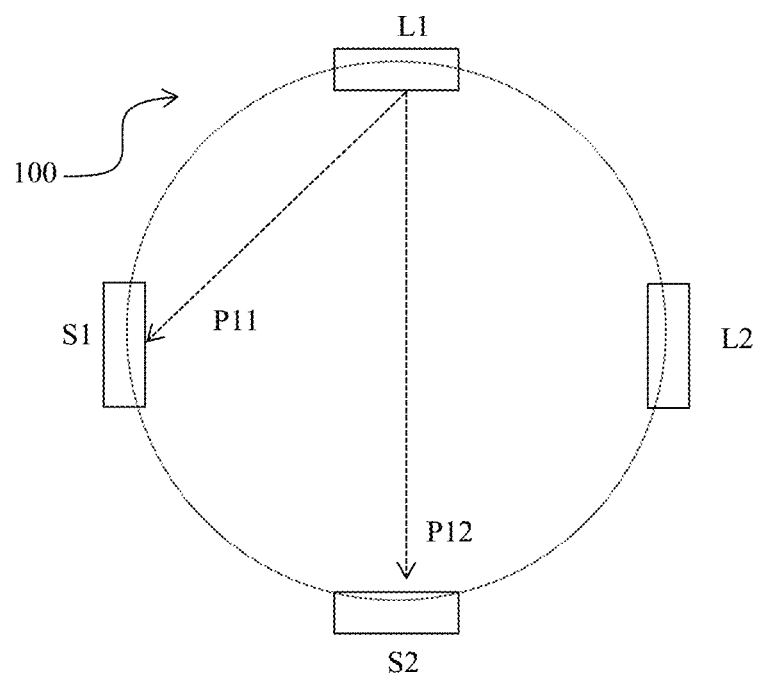
FIG. 16 further shows the second embodiment of FIG. 15.

FIG. 15 and FIG. 16 illustrate yet another embodiment showing how the emitters 104 can be placed adjacent each other on one side of the ring 102 and the sensors 106 placed adjacent each other but on the other side of the ring 102, instead of the configuration in the first embodiment. FIG. 15 shows emitter lighting up first to transmit towards sensor S1 and sensor 2, and FIG. 16 shows emitter L1 lighting up subsequently to transmit towards sensor and sensor S2.

Figure 17:
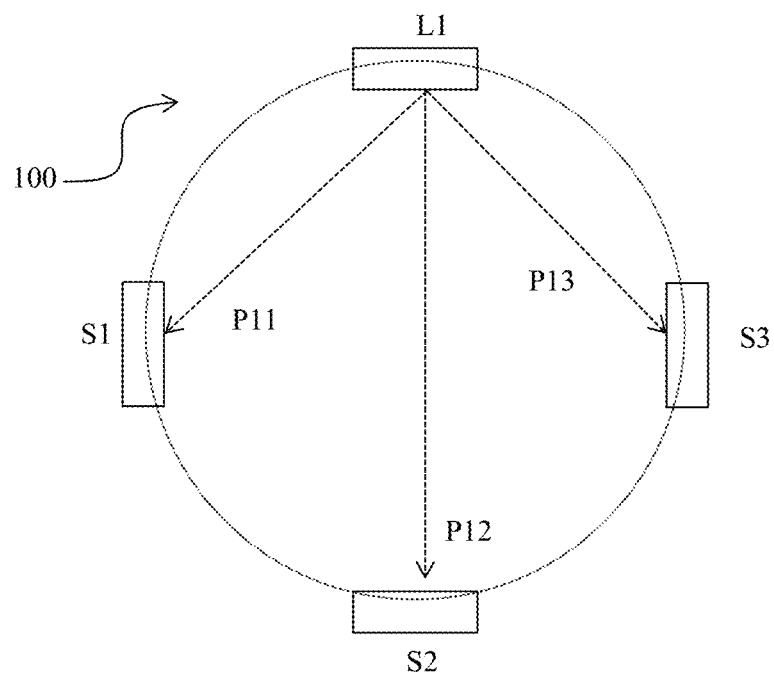
FIG. 17 shows yet a further embodiment of the invention.

In other embodiments, as shown in FIG. 17, a single emitter 104 is used to project infrared light to be detected by three or more sensors 106. This allows three observations to be made with only one emitter 104 and three sensors 106, instead of three emitter and three sensors as in the prior art.

Figure 18:
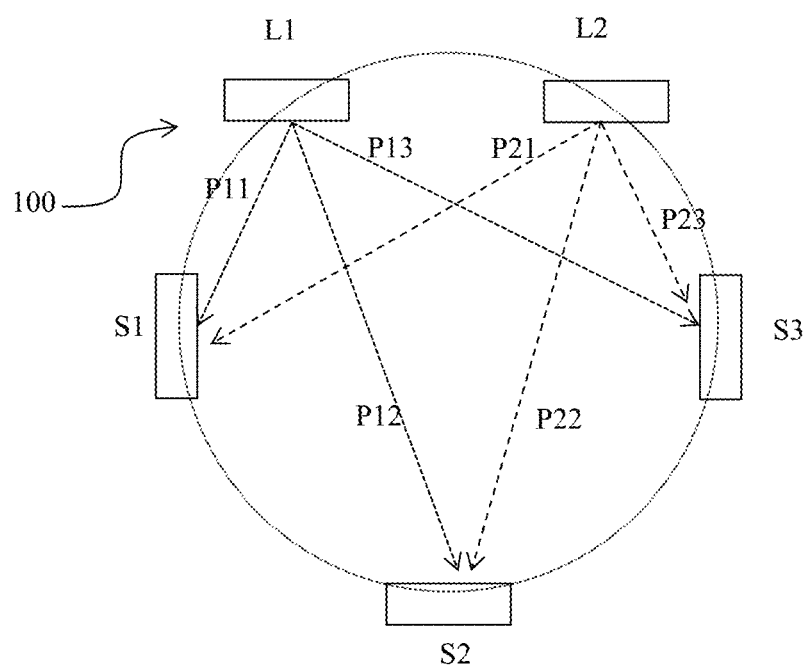
FIG. 18 shows yet a further embodiment of the invention.

FIG. 18 shows how three sensors 106 are used to provide six observations with only two emitters 104. When the emitters 104 emit in consecutive order, the sensors 100 are able to detect six observations. This also provides the advantage that if one of the sensors 106 fail to work, the device 100 as a whole is still functional with two sensors 106 and two emitters 104 providing four observations, which is superior to the use of three observations typical in prior art, in the prior art, each sensor is dedicated to only one emitter and there is therefore no redundancy of observations; the number of observations is the same as the number of sensors 106. Alternatively, in a variation of this embodiment, three emitters 104 and two sensors 106 may be used. In general, use of less emitters 104 with more sensors 106 leads to faster operation than more emitters 104 with less sensors 106, as there is less need of time to wait for each emitter 104 to take its turn.

Figure 19:
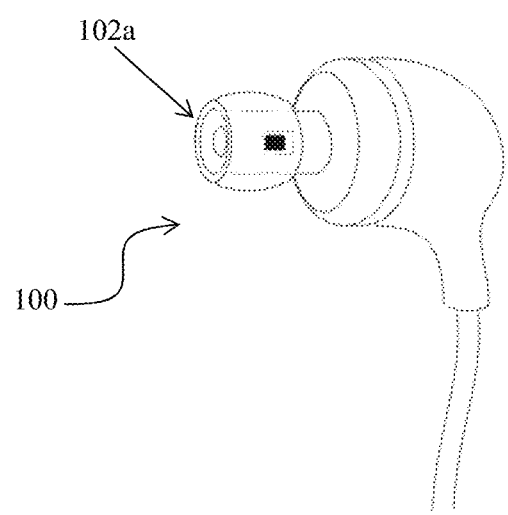
FIG. 19 shows yet a further embodiment of the invention.

Although the device 100 has been described as a ring 102, the device may be provided in other forms such as an ear plug 102a, as shown in FIG. 19. The ear plug typically has emitters 104 arranged on the surface of the ear plug to emit light into the ear of the wearer. The tissues surrounding the ear plug reflects the light back to the ear plug. The ear plug also has sensors 106 arranged on the ear plug surface to detect the reflected light. A drawing of an ear plug is shown in FIG. 19 without illustrating the positions of the emitters and sensors. By the term ear plug, the skilled reader should note that it includes any sufficiently stable attachment to the ear that monitors arterial blood, including ear plug which are insertable into the ear hole, or any attachment which can it just outside the ear hole in the outer ear such as ear phones or any device that can clip to the ear in any way to read light transmission or dispersion in any part of the ear.

Figure 20:
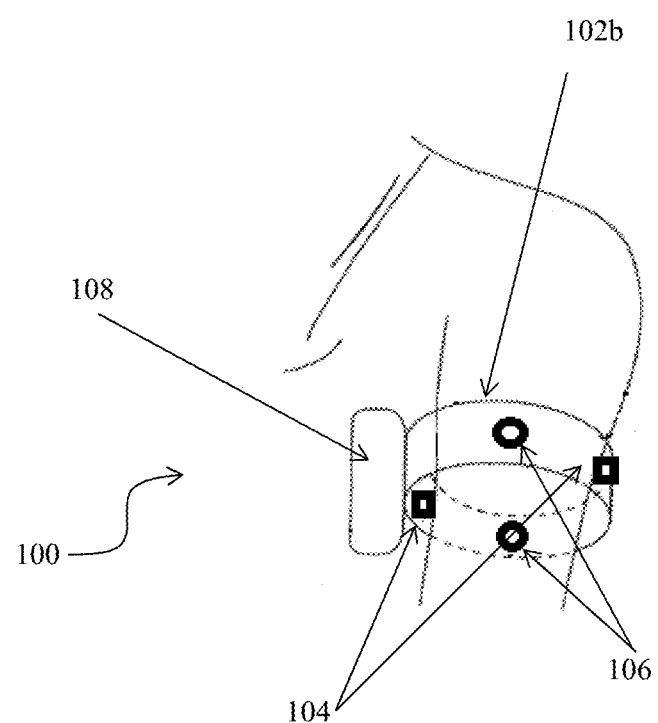
FIG. 20 shows yet a further embodiment of the invention.

Alternatively, the devices 100 can be in the form of an arm band 102b instead of a ring 102, as shown in FIG. 20, in which emitters and sensors are installed for projecting and detecting infrared or other light into the arm of the wear for monitoring heartbeat.

Although infrared light has been described in the embodiments, other wavelengths are possible, as it has been found that blood is capable of absorbing other wavelengths including red, green and blue light.

The embodiments can be implemented in oximeters for detecting oxygen level in blood, which operates by contrasting the ratio of transmission of visible red light to transmission of infrared light. The ratio of the amount of absorbed red light to the amount of absorbed infrared light indicates the amount of oxygen in the blood. Therefore, in embodiments having oximeters functions, there may be an emitter emitting red light to the sensor, and an emitter emitting infrared light to the same sensor which is capable of detecting in both ranges of wavelengths. In this case, the red light emitter and the infrared light emitter take turns to emit light. Alternatively, the emitter is capable of emitting red light and infrared light at the same time, but a separate red light sensor and a separate infrared light sensor detects the different wavelengths selectively and at the same time. Alternatively, the oximeters comprises a set of emitters and sensors as described for emitting and sensing only in red light, and comprises a separate set of emitters and sensors as described for emitting and sensing only in infrared only.

Although a digital signal processing method has been described for treating the infrared signals mathematically, other processing methods or other mathematical treatment is possible. Also an analogue treatment for removing the noise instead of the digital ways described is also possible.

It should be noted that the meaning of a 'pair' of emitter and sensor is merely functionally defined, and each pair of emitter and sensor may be placed immediately next to each other, such as emitter L1 and sensor S3, or emitter L3 and sensor S2 or emitter L2 and sensor S1 of FIG. 10. Alternatively, in other configurations, any pair of emitter and sensor may be placed apart from each other such as the configuration in the embodiment of FIGS. 1, 2 and 3.

The invention claimed is:

1. An apparatus suitable for monitoring arterial blood in a body part,
    the apparatus being suitable for wearing on the body part; and
    the apparatus comprising:
    a support;
    an arrangement of devices around the support;
    the arrangement of devices comprising a plurality of sensors and consisting of a single emitter;
    wherein
    in the sensor arrangement, the plurality of sensors are placed at different angles across from the single emitter so that each sensor is capable of detecting in a different angle light passing through the body part from the single emitter.

2. The apparatus suitable for monitoring arterial blood in a body part, as claimed in claim 1, wherein:
    the apparatus includes a processor configured to detect sensor saturation by ambient light and to disregard light detected passing through the body part by any sensor detected as saturated by ambient light.

3. The apparatus suitable for monitoring arterial blood in a body part, as claimed in claim 1, wherein:
    the support is attachable to the body part, the support having a curved surface; wherein
        the plurality of sensors are distributed along a curvature of the curved surface of the support so as to reduce the likelihood of uniform exposure of the plurality of sensors to ambient light from any one direction at the same time.

4. The apparatus suitable for monitoring arterial blood in a body part, as claimed in claim 3, wherein:
    the support is a ring having the curved surface attachable to the body part.

5. The apparatus suitable for monitoring arterial blood in a body part, as claimed in claim 3, wherein:
    the support is an arm band having the curved surface attachable to the body part.

6. The apparatus suitable for monitoring arterial blood in a body part, as claimed in claim 3, wherein:
    the support is an ear plug.

7. A method of obtaining observations of light transmission to monitor arterial blood in a body part, comprising:
    providing a plurality of sensors and a single emitter onto the body part;

arranging the plurality of sensors and the single emitter around the body part such that the single emitter is placed on one side and the plurality of sensors on another side of the body part across from the single emitter such that light emitted from the single emitter transmits through the body part to arrive at the plurality of sensors in different angles from the single emitter; the method further comprising:

emitting light from the single emitter for transmission through the body part; and sensing light transmitted through the body part and arriving at the plurality of sensors; and obtaining said observations of light transmitted through the body part.

8. The method of obtaining observations of light transmission to monitor arterial blood in a body part, as claimed in claim 7, comprising the further steps of:

determining from said observations whether any one or more of the plurality of sensors as failing to work properly;

disregarding the observations made with the determined one or more of the plurality of sensors failing to work properly; and regarding said observations of any remaining one or more sensors that are working properly to monitor arterial blood.

\* \* \* \* \*